(12) United States Patent
Pratt et al.

(10) Patent No.: US 11,549,906 B2
(45) Date of Patent: Jan. 10, 2023

(54) ELECTRONIC CIRCUIT FOR AN ELECTROCHEMICAL GAS SENSOR

(71) Applicant: HONEYWELL INTERNATIONAL INC., Morris Plains, NJ (US)

(72) Inventors: Keith Francis Edwin Pratt, Portsmouth (GB); Guoliang Li, Shanghai (CN); Jia Wu, Shanghai (CN); Fuyin Liu, Shanghai (CN); Ian Underhay, Bridport (GB); Arek Majczak, Portsmouth (GB)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 401 days.

(21) Appl. No.: 16/711,523

(22) Filed: Dec. 12, 2019

(65) Prior Publication Data
US 2020/0191742 A1    Jun. 18, 2020

(30) Foreign Application Priority Data

Dec. 14, 2018 (CN) ......................... 201811531733.2

(51) Int. Cl.
*G01N 27/404* (2006.01)
*G01N 27/30* (2006.01)
(Continued)

(52) U.S. Cl.
CPC ......... *G01N 27/404* (2013.01); *G01N 27/308* (2013.01); *G01N 27/4065* (2013.01); *G01N 33/0006* (2013.01)

(58) Field of Classification Search
CPC ............ G01N 27/404; G01N 27/4045; G01N 27/4065; G01N 27/308; G01N 33/006
See application file for complete search history.

(56) References Cited

U.S. PATENT DOCUMENTS 4,665,874 A * 5/1987 Kawanabe ........... G01N 27/417
                                                        123/693
4,777,444 A   10/1988 Beijk et al.
(Continued)

OTHER PUBLICATIONS

Article entitled "BJT vs FET (Transistors)" on the Learning about Electronics website published Aug. 15, 2018 (Year: 2018).*
(Continued)

*Primary Examiner* — Alexander S Noguerola
(74) *Attorney, Agent, or Firm* — Alston & Bird LLP

(57) ABSTRACT

Various embodiments disclose an electronic circuit for an electrochemical gas sensor. The electronic circuit comprises a first switching element electrically coupled to a reference terminal of the electrochemical gas sensor and a ground voltage terminal. Further, the electronic circuit comprises a second switching element electrically coupled to a sensing terminal of the electrochemical gas sensor and the ground voltage terminal. In an instance in which the electrochemical gas sensor is powered OFF, the first switching element and the second switching element are configured to electrically couple the reference terminal and the sensing terminal to the ground voltage terminal such that current generated when the sensing electrode and the target gas react while the electrochemical gas sensor is powered OFF flows to the ground voltage terminal and the potential of the reference terminal and the sensing terminal remain the equal.

19 Claims, 8 Drawing Sheets

(51) Int. Cl.
  *G01N 33/00* (2006.01)
  *G01N 27/406* (2006.01)

(56) References Cited

U.S. PATENT DOCUMENTS

| | | | |
|---|---|---|---|
| 4,998,068 A | | 3/1991 | Mckee |
| 5,985,129 A | | 11/1999 | Gough et al. |
| 6,280,604 B1 | * | 8/2001 | Allen ................. G01N 27/4045 205/792 |
| 6,428,684 B1 | | 8/2002 | Warburton |
| 6,599,406 B1 | | 7/2003 | Kawanaka et al. |
| 2016/0178561 A1 | | 6/2016 | Hamer et al. |
| 2018/0321186 A1 | * | 11/2018 | Looney ................. G01N 27/404 |

OTHER PUBLICATIONS

Article entiled "Difference Between an NPN and a PNP Transistor" on the Learning about Electronics website published Aug. 15, 2018 (Year: 2018).*

SGX Sensortech, Electrochemical Sensors Application Note 2 Design of Electronics for Electrochemical Gas Sensors, 2016, [online] [retrieved on Mar. 11, 2020] retrieved from the Internet URL: https://www.google.com/search?rlz=1C1GCEB_enUS853US853&q=Sensortech,+Electrochemical+Sensors+Application+Note+2+Design+of+Electronics+for+Electrochemical+Gas+Sensors, 7 pages.

TI Designs, MSP430 Single-Chip, Portable, Carbon Monoxide (CO) Monitor. 2016, [online] [retrieved Mar. 11, 2020] retrieved from the Internet URL: https://tidesigns.schematics.com/includes/results/P1224, 54 pages.

Abdulrazzaq et al., A Review on High-Resolution CMOS Delay Lines:Towards Sub-Picosecond Jitter Performance, 2016, [online] [retrieved May 6, 2020] retrieved from the Internet URL: https://link.springer.com/article/10.1186/s40064-016-2090-z, 32 pages.

E2V Technologies, Design of Electronics for Electrochemical Gas Sensors—Electrochemical Sensors Application Note 2, 2010, [online] [retrieved May 6, 2020] retrieved from the Internet URL: https://www.cdiweb.com/datasheets/e2v/a1a-ec_sensors_an2_1_v1.pdf, 2 pages.

Extended European Search Report for Patent Application No. 19215442.5, dated Apr. 24, 2020, 10 pages.

Office Action issued in European Application No. 19215442.5 dated Aug. 30, 2021, 4 pages.

* cited by examiner

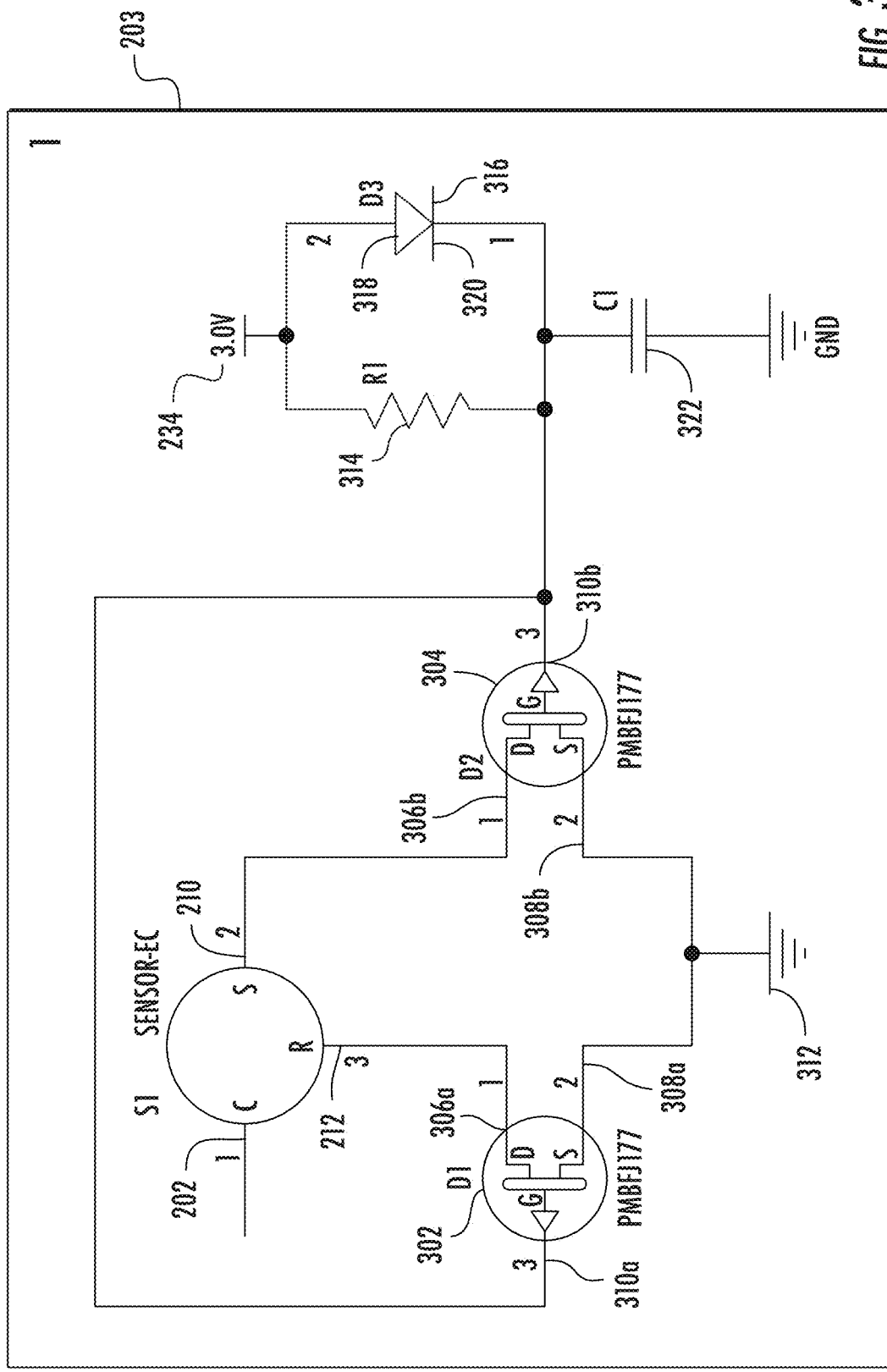

ELECTRONIC CIRCUIT FOR AN ELECTROCHEMICAL GAS SENSOR

CROSS-REFERENCE TO RELATED APPLICATIONS

This specification is based upon and claims the benefit of priority from Chinese patent application number CN 201811531733.2 filed on Dec. 14, 2018, the entire contents of which are incorporated herein by reference.

TECHNOLOGICAL FIELD

Embodiments of the present disclosure relate generally to electrochemical gas sensors and, more particularly, to an electronic circuit for electrochemical gas sensors.

BACKGROUND

Conventional electrochemical gas sensors typically include a reference electrode and a sensing electrode that are in contact with an electrolyte. In operation, the sensing electrode may be coupled with a control and measuring circuit and a voltage source (e.g., battery) that may be configured to apply a predefined bias voltage to the sensing electrode relative to the reference electrode. When the sensing electrode comes into contact with a gas to be detected, e.g., when the gas diffuses in the electrochemical gas sensor, the gas reacts with the sensing electrode, which generates a current at the sensing electrode. A magnitude of the generated current may be indicative of a concentration of the gas detected by the electrochemical gas sensor.

Applicant has identified a number of deficiencies and problems associated with conventional electronic circuits for electrochemical gas sensors. Through applied effort, ingenuity, and innovation, many of these identified problems have been solved by developing solutions that are included in embodiments of the present disclosure, many examples of which are described in detail herein.

BRIEF SUMMARY

Various embodiments illustrated herein disclose an electronic circuit for an electrochemical gas sensor including a first switching element electrically coupled to a reference terminal of the electrochemical gas sensor. The electronic circuit can further include a second switching element electrically coupled to a sensing terminal of the electrochemical gas sensor. In an instance in which the electrochemical gas sensor is powered OFF, the first switching element and the second switching element can be configured to electrically couple the reference terminal and the sensing terminal to a same potential.

Various embodiments illustrated herein disclose a sensing system including an electrochemical gas sensor including a reference electrode and a sensing electrode. In some embodiments, the electrochemical gas sensor is electrically coupled to a voltage source. Further, in some embodiments, the sensing system can include a first transistor including a first terminal electrically coupled to the reference electrode, a second terminal electrically coupled to a ground voltage terminal, and a gate terminal electrically coupled to the ground voltage terminal and to the voltage source. In some embodiments, the sensing system can include a second transistor including a first terminal electrically coupled to the sensing electrode, a second terminal electrically coupled to the ground voltage terminal, and a gate terminal electrically coupled to the ground voltage terminal and to the voltage source. In some embodiments, in an instance in which the electrochemical gas sensor is powered OFF, the gate terminal of the first transistor and the second transistor can be grounded, causing the reference electrode and the reference electrode of the electrochemical gas sensor to connect to the ground voltage terminal through the first transistor and the second transistor, respectively.

In some embodiments, the first terminal of the first transistor can be referred to as "the first terminal," the second terminal of the first transistor can be referred to as "the second terminal," the gate terminal of the first transistor can be referred to as "the first gate terminal," the first terminal of the second transistor can be referred to as "the third terminal," the second terminal of the second transistor can be referred to as "the fourth terminal," and the gate terminal of the second transistor can be referred to as "the second gate terminal."

Thus, in some embodiments, an electronic circuit can be configured to operate at least part of the functions of an electrochemical gas sensor. In some embodiments, the electrochemical gas sensor can include a reference electrode and a sensing electrode, the sensing electrode configured to react with a target gas to generate a current. In some embodiments, the electronic circuit can include at least a first switching element and a second switching element. In some embodiments, the first switching element can be electrically coupled to a reference terminal of the electrochemical gas sensor and a ground voltage terminal. In some embodiments, the second switching element can be electrically coupled to a sensing terminal of the electrochemical gas sensor and the ground voltage terminal. In some embodiments, the first switching element and the second switching element can be configured to, in an instance in which the electrochemical gas sensor is powered OFF, electrically couple the reference terminal and the sensing terminal to the ground voltage terminal such that the current generated when the sensing electrode and the target gas react while the electrochemical gas sensor is powered OFF flows to the ground voltage terminal and a potential at the reference terminal and the potential at the sensing terminal remain equal.

In some embodiments, the first switching element and the second switching element can be configured to, in an instance in which the electrochemical gas sensor is powered OFF, ground the reference electrode and the sensing electrode of the electrochemical gas sensor via the reference terminal and the sensing terminal, respectively, to the ground voltage terminal. In some embodiments, the first switching element corresponds to a first transistor and the second switching element corresponds to a second transistor. In some embodiments, the first transistor can include a first terminal electrically coupled to the ground voltage terminal, and a second terminal electrically coupled to a reference terminal of the electrochemical gas sensor. In some embodiments, the second transistor can include a third terminal electrically coupled to the ground voltage terminal, and a fourth terminal electrically coupled to a sensing terminal of the electrochemical gas sensor.

In some embodiments, the first terminal and the third terminal can correspond to a drain terminal, and the second terminal and the fourth terminal can correspond to a source terminal. In some embodiments, the first terminal and the third terminal can correspond to a source terminal and the second terminal and the fourth terminal can correspond to a drain terminal. In some embodiments, the first transistor can include a first gate terminal and the second transistor can include a second gate terminal. In some embodiments, the first gate terminal can be electrically coupled to the second gate terminal, a voltage source, and the ground voltage terminal. In an instance in which the electrochemical gas sensor is powered OFF, the first gate terminal and the second gate terminal can be grounded, causing the first terminal and the third terminal to short with the second terminal and the fourth terminal, respectively. In an instance in which the electrochemical gas sensor is powered ON, the voltage source can be caused to apply at least a cut-off voltage to the first gate terminal and the second gate terminal, causing the first terminal and the third terminal to disconnect from the second terminal and the fourth terminal, respectively.

In some embodiments, the first gate terminal and the second gate terminal can be electrically coupled to a voltage source through a diode, the diode configured to cause a delay of the electrical coupling of the first gate terminal and the second gate terminal to the voltage source to prevent damage to the electrochemical gas sensor when the electrochemical gas sensor is powered ON. In some embodiments, the first gate terminal and the second gate terminal can be electrically coupled with a voltage source through a resistive element. In some embodiments, the first gate terminal and the second gate terminal can be electrically coupled with the ground voltage terminal through a capacitive element. In some embodiments, the first terminal and the third terminal can be further coupled to a voltage source, such that, in an instance in which the electrochemical gas sensor is powered ON, the voltage source applies a bias voltage at the first terminal and the third terminal to prevent a leakage current from flowing through the first transistor and the second transistor, respectively, while the electrochemical gas sensor is powered ON, and in an instance in which the electrochemical gas sensor is powered OFF, the first terminal and the third terminal are grounded. In some embodiments, the sensing terminal of the electrochemical gas sensor can be electrically coupled to a sensing electrode in the electrochemical gas sensor, and the reference terminal of the electrochemical gas sensor can be electrically coupled to a reference electrode in electrochemical gas sensor.

According to some embodiments, an apparatus for sensing a target gas can include an electrochemical gas sensor and an electrical circuit. In some embodiments, the electrochemical gas sensor can include a reference electrode and a sensing electrode, the sensing electrode configured to generate a current in response to the target gas. In some embodiments, the electrical circuit can include a first transistor comprising a first terminal electrically coupled to the reference electrode, a second terminal electrically coupled to a ground voltage terminal, and a first gate terminal electrically coupled to the ground voltage terminal and through a capacitive element to a voltage source. The electrical circuit can further include a second transistor comprising a third terminal electrically coupled to the sensing electrode, a fourth terminal electrically coupled to the ground voltage terminal, and a second gate terminal electrically coupled to the ground voltage terminal and through the capacitive element to the voltage source. In some embodiments, in an instance in which the electrochemical gas sensor is powered OFF, the first gate terminal and the second gate terminal can be electrically coupled to the ground voltage terminal, causing the reference electrode and the sensing electrode to be electrically coupled to the ground voltage terminal through the first transistor and the second transistor, respectively. In some embodiments, the capacitive element can cause a delay of the electrical coupling of the reference electrode and the sensing electrode to the voltage source to prevent damage to the apparatus when the apparatus is powered ON.

In some embodiments, the electrical circuit can be configured such that, in an instance in which the first gate terminal and the second gate terminal are grounded, the first terminal and the third terminal are shorted with the second terminal and the fourth terminal, respectively, causing the reference electrode and the sensing electrode to connect to the ground voltage terminal. In some embodiments, the electrical circuit can be configured such that, in an instance in which the electrochemical gas sensor is powered ON, the voltage source applies at least a cut-off voltage at the first gate terminal and the second gate terminal, causing the first terminal and the third terminal to disconnect from the second terminal and the fourth terminal, respectively. In some embodiments, the first gate terminal and the second gate terminal can be electrically coupled to the voltage source through a diode. In some embodiments, the first gate terminal and the second gate terminal can be electrically coupled to the voltage source through the resistive element. In some embodiments, the first gate terminal and the second gate terminal can be electrically coupled to the ground voltage terminal through a capacitive element. In some embodiments, the first terminal and the third terminal can be electrically coupled to the voltage source such that, in an instance in which the electrochemical gas sensor is powered ON, the voltage source can apply a bias voltage to the first terminal and the third terminal to prevent a leakage current from flowing through the first transistor and the second transistor while the electrochemical gas sensor is powered ON. The sensing system can be further configures such that, in an instance in which the electrochemical gas sensor is powered OFF, the first terminal and the third terminal are grounded.

Methods described herein can be carried out using any of the devices, circuits, sensors, apparatuses, systems, or components described herein. In some embodiments, a method can be a method of operating an electronic circuit for an electrochemical gas sensor. In some embodiments, the electronic circuit can include a first transistor including a first terminal configured to be electrically coupled to a ground voltage terminal and a second terminal electrically coupled to a reference terminal of the electrochemical gas sensor. In some embodiments, the electronic circuit can further include a second transistor comprising a third terminal configured to be electrically coupled to the ground voltage terminal and a fourth terminal electrically coupled to a sensing terminal of the electrochemical gas sensor. In some embodiments, the electrical circuit can further include a capacitive element configured to delay electrical coupling of at least one of the first transistor and the second transistor to the ground voltage terminal. In any event, a method for operating such electrical circuits for electrochemical gas sensors can include, in an instance in which the electrochemical gas sensor is powered ON, disconnecting the reference terminal and the sensing terminal from the ground voltage terminal. In some embodiments, the method for operating such electrical circuits for electrochemical gas sensors can further include, in an instance in which the electrochemical gas sensor is powered OFF, electrically coupling the reference terminal and the sensing terminal to the ground voltage terminal through the first terminal and the third terminal, respectively, such that a potential of the reference terminal and the potential of the sensing terminal are equal.

Various embodiments illustrated herein disclose a method of operating an electronic circuit for an electrochemical gas sensor. The electronic circuit can include a first transistor having a first terminal electrically coupled to a ground voltage terminal, and a second terminal electrically coupled to a reference terminal of the electrochemical gas sensor. In some embodiments, the electronic circuit can include a second transistor having a first terminal electrically coupled to the ground voltage terminal, and a second terminal electrically coupled to a sensing terminal of the electrochemical gas sensor. The method can include, in an instance in which the electrochemical gas sensor is powered ON, disconnecting the reference terminal and the sensing terminal to a ground voltage terminal. Further, the method can include, in an instance in which the electrochemical gas sensor is powered OFF, connecting the reference terminal and the sensing terminal to the ground voltage terminal such that the reference terminal and the sensing terminal are at a similar or the same voltage.

BRIEF DESCRIPTION OF THE DRAWINGS

The description of the illustrative embodiments can be read in conjunction with the accompanying figures. It will be appreciated that, for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which:

FIGS. 3A-3D illustrate various schematics of electronic circuits for the electrochemical gas sensor, in accordance with at least some of the embodiments described herein.

DETAILED DESCRIPTION

Figure 1:
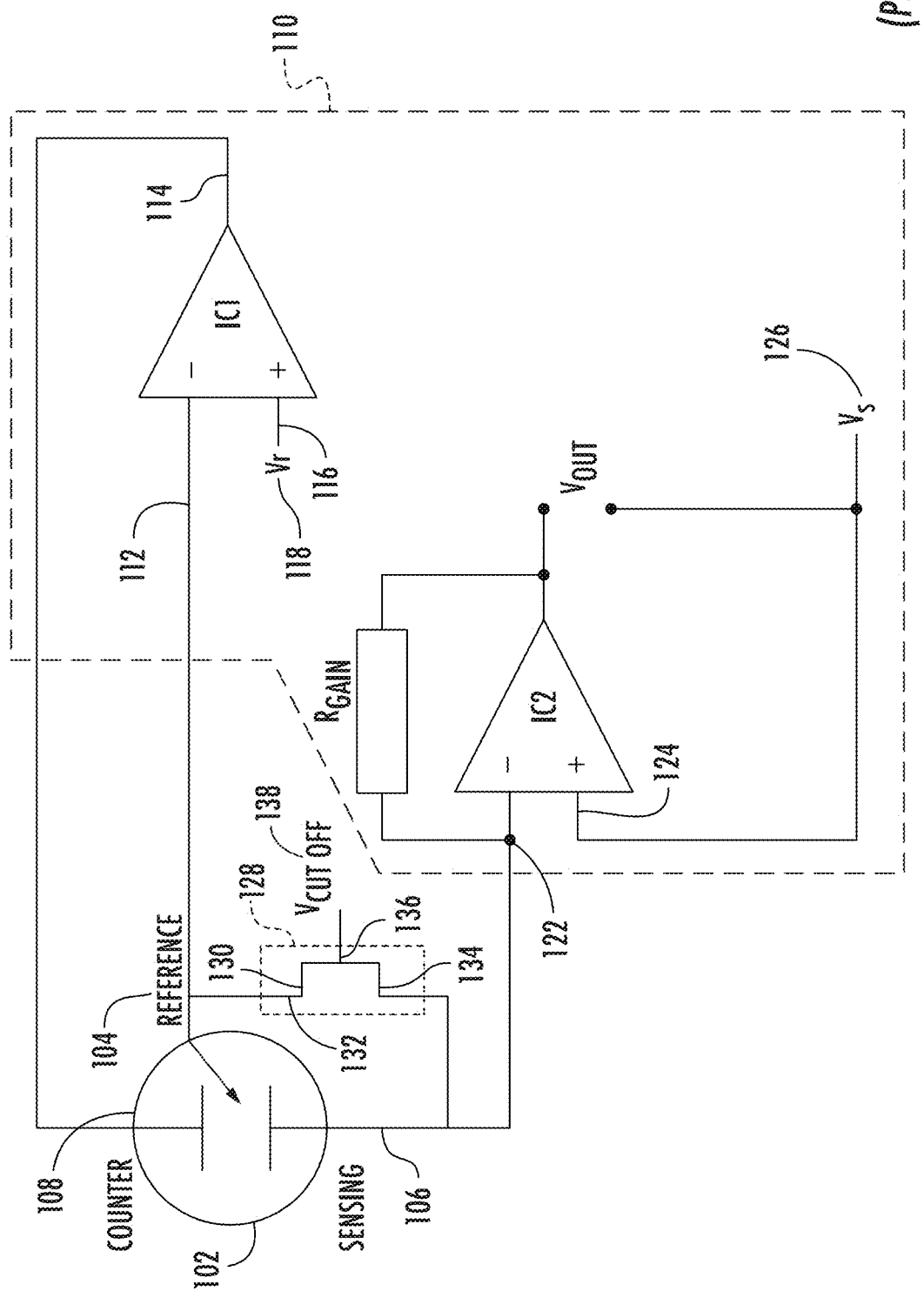
FIG. 1 illustrates a conventional electronic circuit for an electrochemical gas sensor.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations.

The term "comprising" means including but not limited to, and should be interpreted in the manner it is typically used in the patent context. Use of broader terms such as "comprises," "includes," and "having" should be understood to provide support for narrower terms such as "consisting of," "consisting essentially of," and "comprised substantially of."

The phrases "in one embodiment," "according to one embodiment," "in some embodiments," "in some examples," "in some instances," "in that respect," "in some configurations," "in some implementations," and the like generally mean that the particular feature, structure, or characteristic following the phrase may be included in at least one embodiment of the present disclosure, or may be included in more than one embodiment of the present disclosure (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The term "switching element" as used herein corresponds to a switch that is configured to maintain or break electrical path between two electrical components and/or electronic components. In some examples, the switching element may include, but is not limited to, a relay, a transistor, a reed switch, a toggle switch, and/or the like. In some embodiments, the switching element may correspond to a Normally Closed (NC) type switching element or a Normally Open (NO) type switching element. The NC type switching element can be configured to operate in a CLOSED state when the switching element is not connected to a power source and can be configured to operate in an OPEN state when the switching element is connected to the power source. Further, the NO type switching element can be configured to operate in the CLOSED state when the switching element is connected to the power source and can be configured to operate in the OPEN state when the switching element is not connected to the power source. In some embodiments, in the CLOSED state, the switching element can be configured to maintain electrical path between the two electrical/electronic components. Further, in some embodiments, in the OPEN state, the switching element can be configured to break the electrical path between the two electrical/electronic components.

Conventional electrochemical gas sensors often include a reference electrode and a sensing electrode, the sensing electrode configured to generate current when in contact with a gas to be detected (also known as a "target gas", e.g., when the target gas diffuses in the electrochemical gas sensor. To enable detection of the target gas, as discussed above, a bias voltage is applied to the sensing electrode relative to the reference electrode. In some examples, the bias voltage may be zero, e.g., a voltage at the sensing electrode can be equal to the voltage on the reference electrode.

In an instance in which the electrochemical gas sensor is powered OFF, the bias voltage applied at the sensing electrode relative to the reference electrode is removed. Typically, for conventional electrochemical gas sensors, the sensing electrode and the reference electrode are kept floating (i.e., the sensing electrode and the reference electrode are not connected to any other component or to any voltage terminal), when the bias voltage between the sensing electrode and the reference electrode is removed. Therefore, when using conventional electrochemical gas sensors, the target gas around the electrochemical gas sensor may continue to diffuse into the electrochemical gas sensor and react with the sensing electrode when the electrochemical gas sensor is powered OFF. Such reactions between the gas and the sensing electrode when the electrochemical gas sensor is powered OFF may result in generation of background current in the electrolyte that may disturb the reference electrode and therefore is be undesirable.

Conventional methods for avoiding such disturbances in conventional electrochemical gas sensors include shorting the reference electrode and the sensing electrode through a switching element (e.g., a depletion mode P-JFET, such as type J177), as is further described in FIG. 1.

FIG. 1 illustrates a conventional electronic circuit 100 for a electrochemical gas sensor 102. The electrochemical gas sensor 102 includes a reference terminal 104, a sensing terminal 106, and a counter terminal 108. The reference terminal 104, the sensing terminal, and the counter terminal 108 are coupled to a reference electrode, a sensing electrode, and a counter electrode, respectively, in the electrochemical gas sensor 102. The reference terminal 104, the sensing terminal 106, and the counter terminal 108 are electrically coupled to a measurement and control circuitry 110. More particularly, the reference terminal is coupled to a first input terminal 112 of the measurement and control circuitry 110, while the counter terminal 108 is coupled to a first output terminal 114 of the measurement and control circuitry 110. Further, a second input terminal 116 of the measurement and control circuitry 110 is coupled to a first voltage source 118. The first voltage source 118 is configured to apply a reference voltage at the second input terminal 116 of the measurement and control circuitry 110. The measurement and control circuitry 110 is configured to maintain the reference voltage at the reference terminal 104 by varying voltage at the counter terminal 108.

The sensing terminal 106 is electrically coupled to a third input terminal 122 of the measurement and control circuitry 110. A fourth input terminal 124 of the measurement and control circuitry 110 is coupled to a second voltage source 126. The second voltage source 126 is configured to supply a sensing voltage at the fourth input terminal 124 of the measurement and control circuitry 110. Further, the measurement and control circuitry 110 includes a second output terminal 127 through which the voltage at the sensing terminal 106 is measured. A difference between the sensing voltage and the reference voltage corresponds to the bias voltage between the sensing terminal 106 and the reference terminal 104. In some examples, the bias voltage is zero, e.g., the first voltage sources 118 and the second voltage source 126 supply voltages of the same or similar magnitude to the reference terminal 104 and the sensing terminal 106, respectively.

Additionally, the reference terminal 104 and the sensing terminal 106 are coupled through a switching element 128. The switching element 128 may be a Normally Closed "NC" type switching element such that when power (a flow of electric charge such as an electric current) is applied to the switching element 128, the switching element operates in an OPEN state, thereby electrically decoupling the reference terminal 104 and the sensing terminal 106. When power is removed, the switching element 128 operates in a CLOSED state, thereby shorting the reference terminal 104 and the sensing terminal 106.

An example of the NC type switching element 128 may include P-JFET transistor 130. Where the transistor 130 is used as the switching element 128, the reference terminal 104 is coupled to a first terminal 132 of the transistor 130, and the sensing terminal 106 is coupled to a second terminal 134 of the transistor 130. The first terminal 132 of the transistor 130 corresponds to the drain terminal of the transistor 130 and the second terminal 134 of the transistor 130 corresponds to the source terminal of the transistor 130. Further, the transistor 130 includes a gate terminal 136 that is coupled to a third voltage source 138. The third voltage source 138 is configured to supply a cut-off voltage to the gate terminal 136. When the electrochemical gas sensor 102 is powered OFF, the electrochemical gas sensor 202 disconnects from the measurement and control circuitry 110. Further, the transistor 130 disconnects from the third voltage source 138, when the electrochemical gas sensor 102 is powered OFF. Accordingly, the transistor 130 operates in an ON state (because the transistor 130 is a P-JFET) causing the second terminal 134 to become electrically coupled with the first terminal 132, thereby shorting the reference terminal 104 with the sensing terminal 106.

On the other hand, when the electrochemical gas sensor 102 is powered ON, the third voltage source 138 applies the cut-off voltage to the gate terminal 136 of the transistor 130. Accordingly, the transistor 130 operates in an OFF state, causing the second terminal 134 to electrically decouple from the first terminal 132. This further causes the sensing terminal 106 to decouple from the reference terminal 104. Further, when the electrochemical gas sensor 102 is powered ON, the reference terminal 104 and the sensing terminal 106 connect to the measurement and control circuitry 110.

During operation of the electrochemical gas sensor 102, a magnitude of a voltage provided by the first voltage source 118 and the second voltage source 126 may optionally be modulated in order to improve sensitivity of the electrochemical gas sensor 102, or to perform a diagnostic function on either the main sensing electrode or a counter electrode. Further, the bias voltage may be varied to electrochemically modify the sensing electrode surface, for example cleaning contaminants from the electrode. Such voltage modulation may cause voltage variation at the first terminal 132 and/or the second terminal 134 of the transistor 130, which may further cause the transistor 130 to switch to the ON state. As discussed, in the ON state, the first terminal 132 becomes electrically coupled with the second terminal 134, thereby shorting the reference terminal with the sensing terminal, while the electrochemical gas sensor 102 is powered ON. Such scenarios are undesirable. Thus, there is a long-felt need in the industry for an improved electronic circuit for electrochemical gas sensors that doesn't lead to these undesirable conditions.

There is also a long-felt need in the industry for continued miniaturization of electrochemical gas sensors, meaning, in part, that it is desirable to operate the electrochemical gas sensor at lower voltages. While some electrochemical gas sensors and operational amplifiers are capable of operating at lower voltages, conventional transistors, such as the transistor 130, are unable to operate at lower voltages. For example, the gate-source cutoff voltage of a J177 transistor can be as high as 2.5 volts.

In accordance with embodiments of the present disclosure, an electronic circuit for the electrochemical gas sensor is disclosed hereinbelow. In some embodiments, the electronic circuit includes a first switching element and a second switching element. In some embodiments, the first switching element and the second switching element may correspond to an NC type switching element that is configured to operate in a CLOSED or ON state when power is not applied on the switching element. Further, when power is applied to the NC type switching element, the switching element operates in an OPEN or OFF state. Some examples of the switching element may include, but are not limited to, a transistor.

In some embodiments, the first switching element and the second switching element are electrically coupled to a reference terminal and a sensing terminal of the electrochemical gas sensor, respectively. Further, the first switching element and the second switching element can be coupled to a voltage terminal. In some embodiments, the voltage terminal can correspond to an electrical terminal that is maintained at a predefined voltage or potential. For example, in some embodiments, the voltage terminal may be maintained at a ground voltage.

When the electrochemical gas sensor is to be operated, the bias voltage can be maintained between the reference terminal and the sensing terminal. Further, when the electrochemical gas sensor is to be operated, the cut-off voltage can be applied at the first switching element and the second switching element, causing the first switching element and the second switching element to operate in the OFF state. Without wishing to be bound by any particular theory, since the reference terminal and the sensing terminal are connected to different switching elements, voltage variations at the reference terminal and/or the sensing terminal may only affect the respective switching element. Thus, shorting of the reference terminal with the sensing terminal, while the electrochemical gas sensor is powered ON, is avoided.

In some embodiments, when the electrochemical gas sensor is powered OFF, the cut-off voltage is removed from the first switching element and the second switching element, causing the first switching element and the second switching element to operate in the ON state. When the first switching element and the second switching element operate in the ON state, the first switching element and the second switching element, respectively, can connect the reference terminal and the sensing terminal of the electrochemical gas sensor to the voltage terminal. Accordingly, in some embodiments, when the electrochemical gas sensor is powered OFF, the sensing terminal and the reference terminal are at a similar or the same voltage. In some embodiments, where the predefined voltage potential corresponds to the ground voltage, the reference terminal and the sensing terminal of the electrochemical gas sensor are grounded when the electrochemical gas sensor is powered OFF. Without wishing to be bound by any particular theory, by grounding the reference terminal and the sensing terminal, any generated background current is grounded while the electrochemical gas sensor is powered OFF. This avoids generation of potential at the terminals (e.g., sensing terminal) of the electrochemical gas sensor.

Further, in some embodiments, the sensing system can include a first transistor including a first terminal electrically coupled to the reference electrode, a second terminal electrically coupled to a ground voltage terminal, and a gate terminal electrically coupled to the ground voltage terminal and to the voltage source. In some embodiments, the sensing system can include a second transistor including a first terminal electrically coupled to the sensing electrode, a second terminal electrically coupled to the ground voltage terminal, and a gate terminal electrically coupled to the ground voltage terminal and to the voltage source. In some embodiments, in an instance in which the electrochemical gas sensor is powered OFF, the gate terminal of the first transistor and the second transistor can be grounded, causing the reference electrode and the reference electrode of the electrochemical gas sensor to connect to the ground voltage terminal through the first transistor and the second transistor, respectively.

In some embodiments, the first terminal of the first transistor can be referred to as "the first terminal," the second terminal of the first transistor can be referred to as "the second terminal," the gate terminal of the first transistor can be referred to as "the first gate terminal," the first terminal of the second transistor can be referred to as "the third terminal," the second terminal of the second transistor can be referred to as "the fourth terminal," and the gate terminal of the second transistor can be referred to as "the second gate terminal."

Thus, in some embodiments, an electronic circuit can be configured to operate at least part of the functions of an electrochemical gas sensor. In some embodiments, the electrochemical gas sensor can include a reference electrode and a sensing electrode, the sensing electrode configured to react with a target gas to generate a current. In some embodiments, the electronic circuit can include at least a first switching element and a second switching element. In some embodiments, the first switching element can be electrically coupled to a reference terminal of the electrochemical gas sensor and a ground voltage terminal. In some embodiments, the second switching element can be electrically coupled to a sensing terminal of the electrochemical gas sensor and the ground voltage terminal. In some embodiments, the first switching element and the second switching element can be configured to, in an instance in which the electrochemical gas sensor is powered OFF, electrically couple the reference terminal and the sensing terminal to the ground voltage terminal such that the current generated when the sensing electrode and the target gas react while the electrochemical gas sensor is powered OFF flows to the ground voltage terminal and a potential at the reference terminal and the potential at the sensing terminal remain equal.

In some embodiments, the first switching element and the second switching element can be configured to, in an instance in which the electrochemical gas sensor is powered OFF, ground the reference electrode and the sensing electrode of the electrochemical gas sensor via the reference terminal and the sensing terminal, respectively, to the ground voltage terminal. In some embodiments, the first switching element corresponds to a first transistor and the second switching element corresponds to a second transistor. In some embodiments, the first transistor can include a first terminal electrically coupled to the ground voltage terminal, and a second terminal electrically coupled to a reference terminal of the electrochemical gas sensor. In some embodiments, the second transistor can include a third terminal electrically coupled to the ground voltage terminal, and a fourth terminal electrically coupled to a sensing terminal of the electrochemical gas sensor.

In some embodiments, the first terminal and the third terminal can correspond to a drain terminal, and the second terminal and the fourth terminal can correspond to a source terminal. In some embodiments, the first terminal and the third terminal can correspond to a source terminal and the second terminal and the fourth terminal can correspond to a drain terminal. In some embodiments, the first transistor can include a first gate terminal and the second transistor can include a second gate terminal. In some embodiments, the first gate terminal can be electrically coupled to the second gate terminal, a voltage source, and the ground voltage terminal. In an instance in which the electrochemical gas sensor is powered OFF, the first gate terminal and the second gate terminal can be grounded, causing the first terminal and the third terminal to short with the second terminal and the fourth terminal, respectively. In an instance in which the electrochemical gas sensor is powered ON, the voltage source can be caused to apply at least a cut-off voltage to the first gate terminal and the second gate terminal, causing the first terminal and the third terminal to disconnect from the second terminal and the fourth terminal, respectively.

In some embodiments, the first gate terminal and the second gate terminal can be electrically coupled to a voltage source through a diode, the diode configured to cause a delay of the electrical coupling of the first gate terminal and the second gate terminal to the voltage source to prevent damage to the electrochemical gas sensor when the electrochemical gas sensor is powered ON. In some embodiments, the first gate terminal and the second gate terminal can be electrically coupled with a voltage source through a resistive element. In some embodiments, the first gate terminal and the second gate terminal can be electrically coupled with the ground voltage terminal through a capacitive element. In some embodiments, the first terminal and the third terminal can be further coupled to a voltage source, such that, in an instance in which the electrochemical gas sensor is powered ON, the voltage source applies a bias voltage at the first terminal and the third terminal to prevent a leakage current from flowing through the first transistor and the second transistor, respectively, while the electrochemical gas sensor is powered ON, and in an instance in which the electrochemical gas sensor is powered OFF, the first terminal and the third terminal are grounded. In some embodiments, the sensing terminal of the electrochemical gas sensor can be electrically coupled to a sensing electrode in the electrochemical gas sensor, and the reference terminal of the electrochemical gas sensor can be electrically coupled to a reference electrode in electrochemical gas sensor.

According to some embodiments, an apparatus for sensing a target gas can include an electrochemical gas sensor and an electrical circuit. In some embodiments, the electrochemical gas sensor can include a reference electrode and a sensing electrode, the sensing electrode configured to generate a current in response to the target gas. In some embodiments, the electrical circuit can include a first transistor comprising a first terminal electrically coupled to the reference electrode, a second terminal electrically coupled to a ground voltage terminal, and a first gate terminal electrically coupled to the ground voltage terminal and through a capacitive element to a voltage source. The electrical circuit can further include a second transistor comprising a third terminal electrically coupled to the sensing electrode, a fourth terminal electrically coupled to the ground voltage terminal, and a second gate terminal electrically coupled to the ground voltage terminal and through the capacitive element to the voltage source. In some embodiments, in an instance in which the electrochemical gas sensor is powered OFF, the first gate terminal and the second gate terminal can be electrically coupled to the ground voltage terminal, causing the reference electrode and the sensing electrode to be electrically coupled to the ground voltage terminal through the first transistor and the second transistor, respectively. In some embodiments, the capacitive element can cause a delay of the electrical coupling of the reference electrode and the sensing electrode to the voltage source to prevent damage to the apparatus when the apparatus is powered ON.

In some embodiments, the electrical circuit can be configured such that, in an instance in which the first gate terminal and the second gate terminal are grounded, the first terminal and the third terminal are shorted with the second terminal and the fourth terminal, respectively, causing the reference electrode and the sensing electrode to connect to the ground voltage terminal. In some embodiments, the electrical circuit can be configured such that, in an instance in which the electrochemical gas sensor is powered ON, the voltage source applies at least a cut-off voltage at the first gate terminal and the second gate terminal, causing the first terminal and the third terminal to disconnect from the second terminal and the fourth terminal, respectively. In some embodiments, the first gate terminal and the second gate terminal can be electrically coupled to the voltage source through a diode. In some embodiments, the first gate terminal and the second gate terminal can be electrically coupled to the voltage source through the resistive element. In some embodiments, the first gate terminal and the second gate terminal can be electrically coupled to the ground voltage terminal through a capacitive element. In some embodiments, the first terminal and the third terminal can be electrically coupled to the voltage source such that, in an instance in which the electrochemical gas sensor is powered ON, the voltage source can apply a bias voltage to the first terminal and the third terminal to prevent a leakage current from flowing through the first transistor and the second transistor while the electrochemical gas sensor is powered ON. The sensing system can be further configures such that, in an instance in which the electrochemical gas sensor is powered OFF, the first terminal and the third terminal are grounded.

Methods described herein can be carried out using any of the devices, circuits, sensors, apparatuses, systems, or components described herein. In some embodiments, a method can be a method of operating an electronic circuit for an electrochemical gas sensor. In some embodiments, the electronic circuit can include a first transistor including a first terminal configured to be electrically coupled to a ground voltage terminal and a second terminal electrically coupled to a reference terminal of the electrochemical gas sensor. In some embodiments, the electronic circuit can further include a second transistor comprising a third terminal configured to be electrically coupled to the ground voltage terminal and a fourth terminal electrically coupled to a sensing terminal of the electrochemical gas sensor. In some embodiments, the electrical circuit can further include a capacitive element configured to delay electrical coupling of at least one of the first transistor and the second transistor to the ground voltage terminal. In any event, a method for operating such electrical circuits for electrochemical gas sensors can include, in an instance in which the electrochemical gas sensor is powered ON, disconnecting the reference terminal and the sensing terminal from the ground voltage terminal. In some embodiments, the method for operating such electrical circuits for electrochemical gas sensors can further include, in an instance in which the electrochemical gas sensor is powered OFF, electrically coupling the reference terminal and the sensing terminal to the ground voltage terminal through the first terminal and the third terminal, respectively, such that a potential of the reference terminal and the potential of the sensing terminal are equal.

Figure 2A:
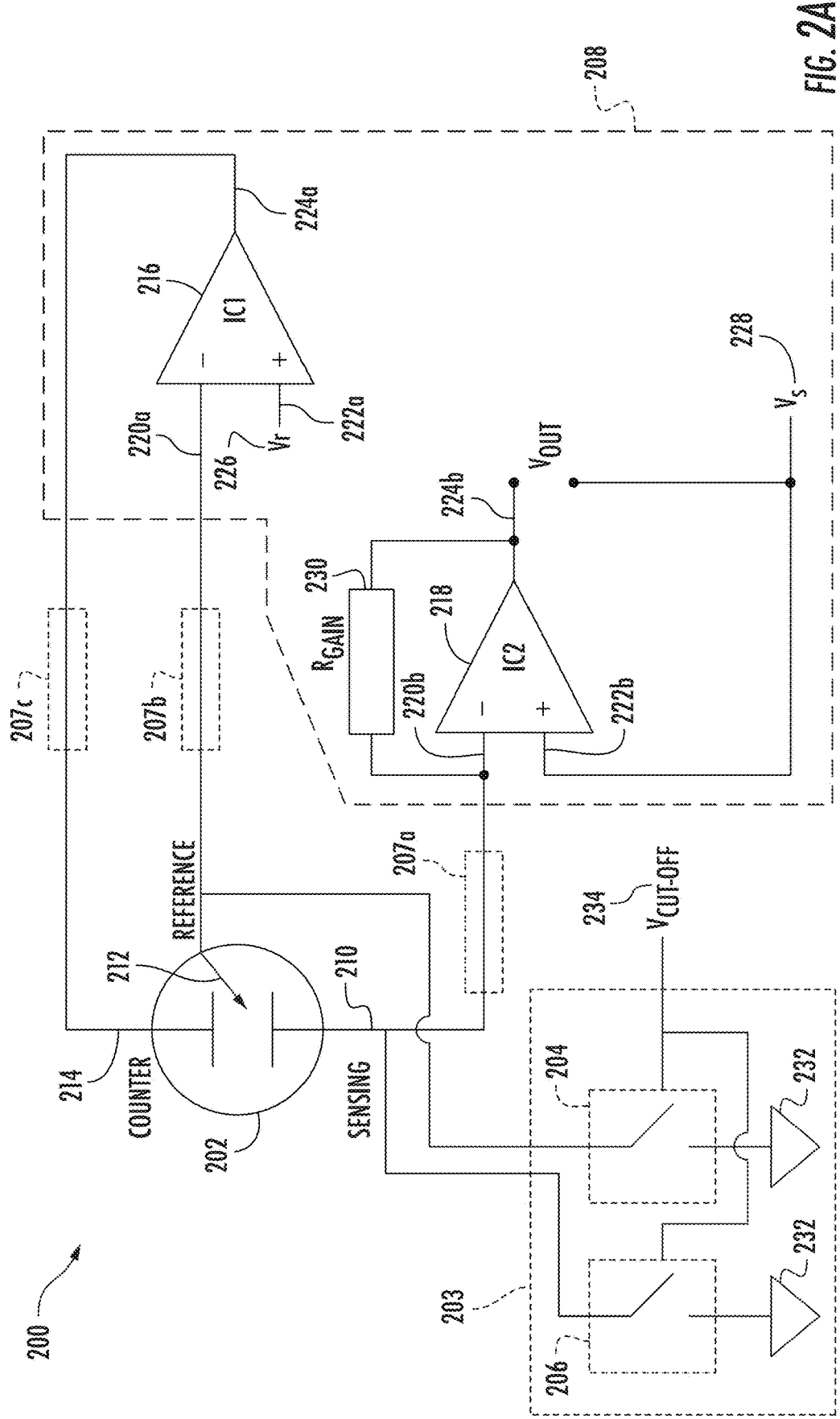
FIGS. 2A and 2B illustrate a schematic diagram of a sensing system, according to one or more embodiments described herein.
Figure 2B:
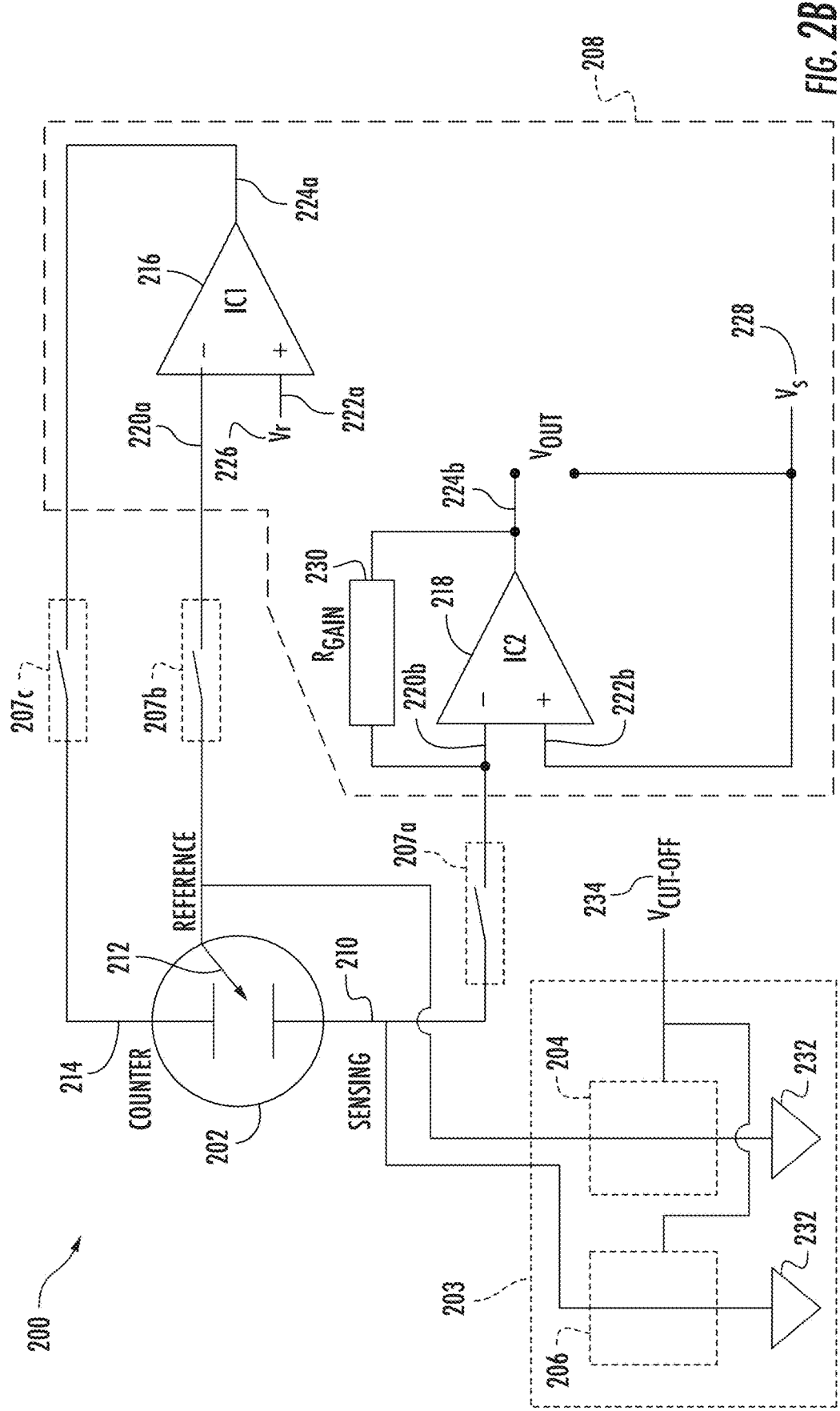

FIGS. 2A and 2B illustrate a schematic diagram of a sensing system 200, according to some embodiments described herein. As shown, the sensing system 200 includes an electrochemical gas sensor 202, an electronic circuit 203, and a measurement and control circuitry 208. The electronic circuit 203 can include a first switching element 204 and a second switching element 206. The electrochemical gas sensor 202 can includes a sensing terminal 210 and a reference terminal 212. In some embodiments, and the electrochemical gas sensor 202 can further include a counter terminal 214. In some embodiments, the sensing terminal 210 can be coupled to a sensing electrode (not shown) in the electrochemical gas sensor 202. Similarly, in some embodiments, the reference terminal 212 and counter terminal 214 can be coupled to the reference electrode and the counter electrode in the housing of the electrochemical gas sensor 202.

In some embodiments, the reference terminal 212, the sensing terminal 210, and/or the counter terminal 214 can be connected to the measurement and control circuitry 208. In some embodiments, the reference terminal 212, the sensing terminal 210, and the counter terminal 214 can be coupled to the measurement and control circuitry 208 through one or more switches 207a, 207b, and 207c, respectively. The one or more switches 207a, 207b, and 207c may correspond to solid state switches that are configured to power ON or power OFF the electrochemical gas sensor 202. For example, to power ON the electrochemical gas sensor 202, the one or more switches 207a, 207b, and 207c can be configured to operate in a CLOSED state, as is illustrated in FIG. 2A. Further, to power OFF the electrochemical gas sensor 202, the one or more switches 207a, 207b, and 207c can be configured to be in OPEN state, as is illustrated in FIG. 2B.

In some embodiments, the measurement and control circuitry 208 can be configured to supply a reference voltage and a sensing voltage to the reference terminal 212 and the sensing terminal 210, respectively, when the sensing system 200 is powered ON. In some embodiments, the measurement and the control circuitry 208 can include a first amplifier 216 and a second amplifier 218. In some embodiments, the first amplifier 216 and the second amplifier 218 may be realized using an operational amplifier (OP-AMP). However, the scope of the disclosure is not limited to using the OP-AMP to realize the first amplifier 216 and the second amplifier 218. In some embodiments, the known transistor circuits may be used as the first amplifier 216 and the second amplifier 218, without departing from the scope of the disclosure.

In some embodiments, the first amplifier 216 and the second amplifier 218 can include a first input terminal 220a and 220b, a second input terminal 222a and 222b, and an output terminal 224a and 224b, respectively. The first input terminal 220a of the first amplifier 216 can be coupled to the reference terminal 212 of the electrochemical gas sensor 202, e.g., through the switch 207b. The second input terminal 222a of the first amplifier 216 can be coupled to a first voltage source 226. In some embodiments, the first voltage source 226 may be configured to apply reference voltage to the second input terminal 222a. Further, the output terminal 224a of first amplifier 216 can be coupled to the counter terminal 214 of the electrochemical gas sensor 202, e.g., through the switch 207c.

The first input terminal 220b of the second amplifier 218 can be coupled to the sensing terminal 210 of the electrochemical gas sensor 202, e.g., through the switch 207a. The second input terminal 222b of the second amplifier 218 can be coupled to a second voltage source 228. In some embodiments, the second voltage source 228 can be configured to apply a sensing voltage to the second input terminal 222b of the second amplifier 218. Further, the output terminal 224b of the second amplifier 218 can be coupled to the first input terminal 220a, e.g., through a resistive element 230.

In some embodiments, if the first amplifier 216 and the second amplifier 218 are realized using op-amps, the voltage at the first input terminal 220a and 220b of the first amplifier 216 and the second amplifier 218, respectively, can be similar to, substantially equal to, or equal to the voltage at the second input terminal 222a and the 222b of the first amplifier 216 and the second amplifier 218, respectively. Accordingly, the voltage at the first input terminal 220a of the first amplifier 216 can be similar to, substantially equal to, or equal to the reference voltage. Further, the voltage at the first input terminal 220b of the second amplifier 218 can be similar to, substantially equal to, or equal to the sensing voltage. In some embodiments, if the sensing terminal 210 and the reference terminal 212 of the electrochemical gas sensor 202 are coupled to the first input terminal 220a and the first input terminal 220b, respectively, the sensing voltage and the reference voltage can be applied to the sensing terminal 210 and the reference terminal 212, respectively.

In some embodiments, additionally, the reference terminal 212 and the sensing terminal 210 can be electrically coupled to the first switching element 204 and the second switching element 206, respectively. In some embodiments, the first switching element 204 and the second switching element 206 can be further coupled to a ground voltage terminal 232. In some embodiments, the ground voltage terminal 232 may correspond to an electrical terminal, e.g., an electrical terminal that is maintained at a predefined voltage. For example, the ground voltage terminal 232 may be maintained at a ground voltage, as is further described in conjunction with FIGS. 3a-3d. In some embodiments, the first switching element 204 and the second switching element 206 can be further electrically coupled to a third voltage source 234. The third voltage source 234 may be configured to supply a cut-off voltage to the first switching element 204 and the second switching element 206. In some embodiments, the first switching element 204 and the second switching element 206 can be configured to connect the reference terminal 212 and the sensing terminal 210 to the ground voltage terminal 232, e.g., when the first switching element 204 and the second switching element 206 operate in a CLOSED state. Further, in some embodiments, the first switching element 204 and/or the second switching element 206 can be configured to disconnect the reference terminal 212 and/or the sensing terminal 210 from the ground voltage terminal 232, e.g., when the first switching element 204 and/or the second switching element 206 operate in an OPEN state. In some embodiments, the first switching element 204 and the second switching element 206 may operate in the OPEN state when the first switching element 204 and the second switching element 206 receives the cut-off voltage from the first voltage source 226. In some embodiments, the first switching element 204 and the second switching element 206 may receive the cut-off voltage when the sensing system 200 is powered ON. Further, in some embodiments, the first switching element 204 and the second switching element 206 may operate in the CLOSED state when the first switching element 204 and the second switching element 206 do not receive the cut-off voltage from the first voltage source 118. In some embodiments, the first switching element 204 and the second switching element 206 do not receive the cut-off voltage when the sensing system 200 is powered OFF.

In some embodiments, the first voltage source 226, the second voltage source 228, and the third voltage source 234 may correspond to a single voltage source that is configured to supply the reference voltage, the sensing voltage, and the ground voltage terminal 232. Some examples of the single voltage source may include, but not limited to, a battery, a Switched-Mode Power Supply (SMPS), and/or the like.

In operation, when the sensing system 200 is powered ON (e.g., in response to a user of the electrochemical gas sensor 202 pressing a power button (not shown), in response to receiving a signal indicative of a command to power ON, in response to feedback from a sensor or from the electrical circuit itself, etc.), the one or more switches 207a, 207b, and 207c may operate in a CLOSED state. Accordingly, in some embodiments, the first voltage source 226, the second voltage source 228, and the third voltage source 234 may supply the reference voltage to the reference terminal 212, the sensing voltage to the sensing terminal 210, and the cut-off voltage to the first switching element 204 and the second switching element 206, respectively. According to some embodiments, in an instance in which the cut-off voltage is applied to the first switching element 204 and the second switching element 206, the first switching element 204 and the second switching element 206 may operate in the OPEN state. Further, as discussed, in the OPEN state, the first switching element 204 and the second switching element 206 may decouple the reference terminal 212 and the sensing terminal 210, respectively, from the ground voltage terminal 232. Accordingly, in some embodiments, the reference terminal 212 may receive the reference voltage from the first amplifier 216. Additionally or alternatively, in some embodiments, the sensing terminal 210 may receive the sensing voltage from the second amplifier 218. In some embodiments, the difference between the reference voltage and the sensing voltage may correspond, in part or in full, to a bias voltage between the reference terminal 212 and the sensing terminal 210.

When gas diffuses in the electrochemical gas sensor 202, the gas reacts with the sensing electrode coupled to the sensing terminal 210 to generate a current. In some embodiments, the generated current causes a change in the voltage at the second output terminal 224b of the second amplifier 218, e.g., a voltage swing. The magnitude of voltage swing may be indicative of the concentration of gas detected by the sensing electrode (the sensing electrode being coupled, according to some embodiments, to the sensing terminal 210).

In some embodiments, in an instance in which the sensing system 200 is powered OFF, the one or more switches 207a, 207b, and 207c operate in the OPEN state, as is illustrated in FIG. 2B. Accordingly, in such embodiments, the first voltage source 226, the second voltage source 228, and the third voltage source 234 can disconnect from the electrochemical gas sensor 202. Consequently, the first switching element 204 and the second switching element 206 do not receive the cut-off voltage. As discussed, when the first switching element 204 and the second switching element 206 do not receive the cut-off voltage, the first switching element 204 and the second switching element 206 can operate in the CLOSED state, thereby, connecting the reference terminal 212 and the sensing terminal 210 to the ground voltage terminal 232. Since both the reference terminal 212 and the sensing terminal 210 are connected to the ground voltage terminal 232 (i.e., the reference terminal 212 and the sensing terminal 210 are at the same potential), any background current (e.g., current generated due to a reaction between the sensing electrode and the diffused gas) is able to flow through the electrochemical gas sensor 202 to the voltage terminal. This avoids a shift in the potential at the sensing electrode 210.

In some embodiments, the first switching element 204 and/or the second switching element 206 may be, include, or comprise a transistor such as a P-JFET, as is illustrated in FIGS. 3A-3D. However, the scope of the disclosure is not limited to embodiments in which the first switching element 204 and/or second switching element 206 are, include, or comprise P-JFET transistors. For example, in some embodiments, the first switching element 204 and/or the second switching element 206 may be, include, or comprise a p-type metal-oxide-semiconductor field-effect transistor (P-MOSFET). In other embodiments, the first switching element 204 and/or the second switching element 206 can be, include, or comprise any other suitable switch, e.g., many types of NC type switches. In alternative embodiments, the first switching element 204 and/or the second switching element 206 may be realized using n-type transistors, without departing from the scope of the disclosure.

In some examples, the scope of the disclosure is not limited to the aforementioned circuit of the sensing system 200. In alternative embodiment, the sensing system 200 can include additional electrical/electronic components (e.g., additional resistive elements, additional capacitive elements, and/or the like).

FIGS. 3A-3D illustrate various schematics of an electronic circuit 203 for the electrochemical gas sensor 202, in accordance with one or more embodiments described herein.

Referring to FIG. 3A, the electronic circuit 203 includes a first transistor 302 and a second transistor 304. The first transistor 302 can have a first terminal 306a, a second terminal 308a, and a gate terminal 310a. Similarly, in some embodiments, the second transistor 304 can include a first terminal 306b, a second terminal 308b, and a gate terminal 310b. In some embodiments, the first terminal 306a and/or the first terminal 306b of the first transistor 302 and/or the second transistor 304, respectively, can correspond to the drain terminal of the first transistor 302 and/or the second transistor 304. Further, in some embodiments, the second terminal 308a and/or the second terminal 308b of the first transistor 302 and/or the second transistor 304, respectively, correspond to the source terminal of the first transistor 302 and/or the second transistor 304. In some embodiments, the first terminal 306a and/or the first terminal 306b and the second terminal 308a and/or the second terminal 308b of the first transistor 302 and/or the second transistor 304, respectively, are interchangeable. Hereinafter, the first terminal 306a of the first transistor 302 and the first terminal 306b of the second transistor 304 are referred to as the drain terminal of, respectively, the first transistor 302 and the second transistor 304. Likewise, hereinafter, the second terminal 308a of the first transistor 302 and second terminal 308b of the second transistor 304 have been referred to as the source terminal of, respectively, the first transistor 302 and the second transistor 304. However, such references in any embodiment described herein are not meant to limit the function of any terminal of any transistor.

In some embodiments, the first terminal 306a of the first transistor 302 can be referred to as "the first terminal 306a," the second terminal 308a of the first transistor 302 can be referred to as "the second terminal 308a," the gate terminal 310a of the first transistor 302 can be referred to as "the first gate terminal 310a," the first terminal 306b of the second transistor 304 can be referred to as "the third terminal 306b," the second terminal 308b of the second transistor 304 can be referred to as "the fourth terminal 308b," and the gate terminal 310b of the second transistor 304 can be referred to as "the second gate terminal 310b."

In some embodiments, the drain terminal 306a of the first transistor 302 can be coupled to the reference terminal 212 of the electrochemical gas sensor 202. Further, in some embodiment, the source terminal 308a of the first transistor 302 can be coupled to a ground voltage terminal 312. The ground voltage terminal can be maintained at or near a ground voltage. Further, the gate terminal 310a of the first transistor 302 can be coupled to the third voltage source 234, e.g., through a resistive element 314 and/or a diode 316. In some embodiments, the diode 316 and/or the resistive element 314 can be coupled together in any suitable configuration, e.g., a parallel configuration in which a positive terminal 318 of the diode 316 is coupled to the third voltage source 234 and a negative terminal 320 of the diode 316 is coupled to the gate terminal 310a of the first transistor 302. Further, in some embodiments, the gate terminal 310a of the first transistor 302 can be coupled to the ground voltage terminal 312, e.g., through a capacitive element 322. Additionally, the gate terminal 310a of the first transistor 302 can be coupled to the second transistor 304, e.g., via the gate terminal 310b of the second transistor 304. The drain terminal 306b of the second transistor 304 can be coupled to the sensing terminal 210 of the electrochemical gas sensor 202. Further, the source terminal 308b of the second transistor 304 can be coupled to the ground voltage terminal 312.

For brevity, the measurement and control circuitry 208 is not illustrated in FIGS. 3A-3D. However, the reference terminal 212, the sensing terminal 210, and/or the counter terminal 214 of the electrochemical gas sensor 202 can be coupled to the measurement and control circuitry 208 through the one or more switches, e.g., via switches 207a, 207b, and 207c, respectively.

In operation, when the sensing system 200 is powered ON, the third voltage source 234 can be configured to supply the cut off voltage to the gate terminal 310a of the first transistor 302 and/or the gate terminal 310b of the second transistor 304. In some embodiments in which the first transistor 302 and/or the second transistor 304 are P-JFET, on application of the cut-off voltage on the respective gate terminals (310a and 310b) the first transistor 302 and the second transistor 304 can be configured to operate in OFF state. In some embodiments, in the OFF state, the first transistor 302 and/or the second transistor 304 can electrically decouple the drain terminal (308a, 308b) and the source terminal (306a, 306b), respectively. Accordingly, in some embodiments, the first transistor 302 can be caused to decouple the reference terminal 212 and the second transistor 304 can be caused to decouple the sensing terminal 210. In some embodiments, one or both of the first transistor 302 and the second transistor 304 can be configured to decouple the reference terminal 212 and/or the sensing terminal 210 from the ground voltage terminal 312. In some embodiments, decoupling the electrochemical gas sensor 202 from the ground voltage terminal 312 may allow the electrochemical gas sensor 202 to couple with the measurement and control circuitry 208 (as the one or more switches 207a, 207b, and 207c can be configured to operate in CLOSED state when the sensing system 200 is powered ON). For example, in some embodiments, upon coupling the electrochemical gas sensor 202 with the measurement and control circuitry 208, the measurement and control circuitry 208 can apply the bias voltage at the sensing terminal 210 relative to the reference terminal 212. In other words, the difference between the reference voltage and the sensing voltage can be supplied by the measurement and control circuitry 208. Thereafter, the electrochemical gas sensor 202 may operate as described above with respect to FIGS. 2A-2B. For example, when gas diffuses in the electrochemical gas sensor 202, the gas may react with the sensing electrode, e.g., the sensing electrode coupled to the sensing terminal 210, to generate a current. The generated current can cause the voltage at the output terminal 224b of the second amplifier 218 (in the measurement and control circuitry 208) to change, e.g., a voltage swing. The magnitude of voltage swing can be indicative of the concentration of gas detected by the sensing electrode (coupled to the sensing terminal 210). In some embodiments, the electrochemical gas sensor 202 can include means for measuring the voltage and interpreting the voltage change as a concentration of the target gas. In some embodiments, the electrochemical gas sensor 202 can include a processor (not shown) configured to measure the voltage change (e.g., voltage swing) and determine the concentration of the gas detected by the sensing electrode.

In some embodiments, during operation of the electrochemical gas sensor 202, the bias voltage at the sensing terminal 210 relative to the reference terminal 212 can be varied, for example to improve the sensitivity of the electrochemical gas sensor 202. In some embodiments, the variation in the bias voltage may be attained by varying sensing voltage and/or the reference voltage. In some embodiments, the processor can be utilized to vary the reference voltage and/or the sensing voltage to vary the bias voltage between the sensing terminal 210 and the reference terminal 212. Without wishing to be bound by any particular theory, varying the bias voltage may, in some scenarios, cause the voltage at the drain terminal 306a, 306b of the first transistor 302 and/or the second transistor 304 to change. However, since the source terminal 306a of the first transistor 302 and the source terminal 306b of the second transistor 304 are grounded, the first transistor 302 and the second transistor 304 never switches to the ON state while the sensing system 200 is powered ON. Accordingly, for some embodiments, while the sensing system 200 is powered ON, the reference terminal 212 and the sensing terminal 210 may not get shorted due to variation in the bias voltage between the reference terminal 212 and the sensing terminal 210.

When the sensing system 200 is powered OFF, the gate terminals 310a and 310b of the first transistor 302 and the second transistor 304, respectively, at least in some embodiments, may couple to the ground voltage terminal 312 (as the third voltage source 234 is disconnected from the electronic circuit 203). In some embodiments wherein the first transistor 302 and the second transistor 304 are P-JFET, the first transistor 302 and the second transistor 304 can operate in the ON state when the gate terminals 310a and 310b of the first transistor 302 and the second transistor 304, respectively, couple or are coupled to the ground voltage terminal 312. Further, as discussed with regard to some embodiments, when the first transistor 302 and the second transistor 304 operate in the ON state, the source terminals 308a and 308b of the first transistor 302 and the second transistor 304 can connect to the drain terminals 306a and the 306b, respectively. Accordingly, the reference terminal 212 can connect to the ground voltage terminal 312. Similarly, the sensing terminal 210 can also be coupled to the ground voltage terminal 312. Consequently, any background current (due to chemical reaction between the sensing electrode and the gas), while the sensing system 200 is powered OFF, is allowed to flow to the ground voltage terminal 312 without causing a voltage to be generated between the two electrodes, and the negative consequences thereof are avoided.

In some embodiments, when the sensing system 200 is powered OFF, the electronic circuit 203 and the electrochemical gas sensor 202 may have some transient voltages and transient currents. For some embodiments, if the reference terminal 212 and the sensing terminal 210 of the electrochemical gas sensor 202 are connected to the ground voltage terminal 312 as soon as the sensing system 200 is powered OFF, the transient voltages and the transient current may damage the electrochemical gas sensor 202. In some embodiments, the diode 316 and/or the capacitive element 322 in the electronic circuit 203 may delay the switching of the first transistor 302 and the second transistor 304 to ON state, thereby delaying the coupling of the reference terminal 212 and the sensing terminal 210 with the ground voltage terminal 312. Thereby, for such embodiments, the electrochemical gas sensor 202 is not disturbed by the transient voltages and the transient current.

Figure 3B:
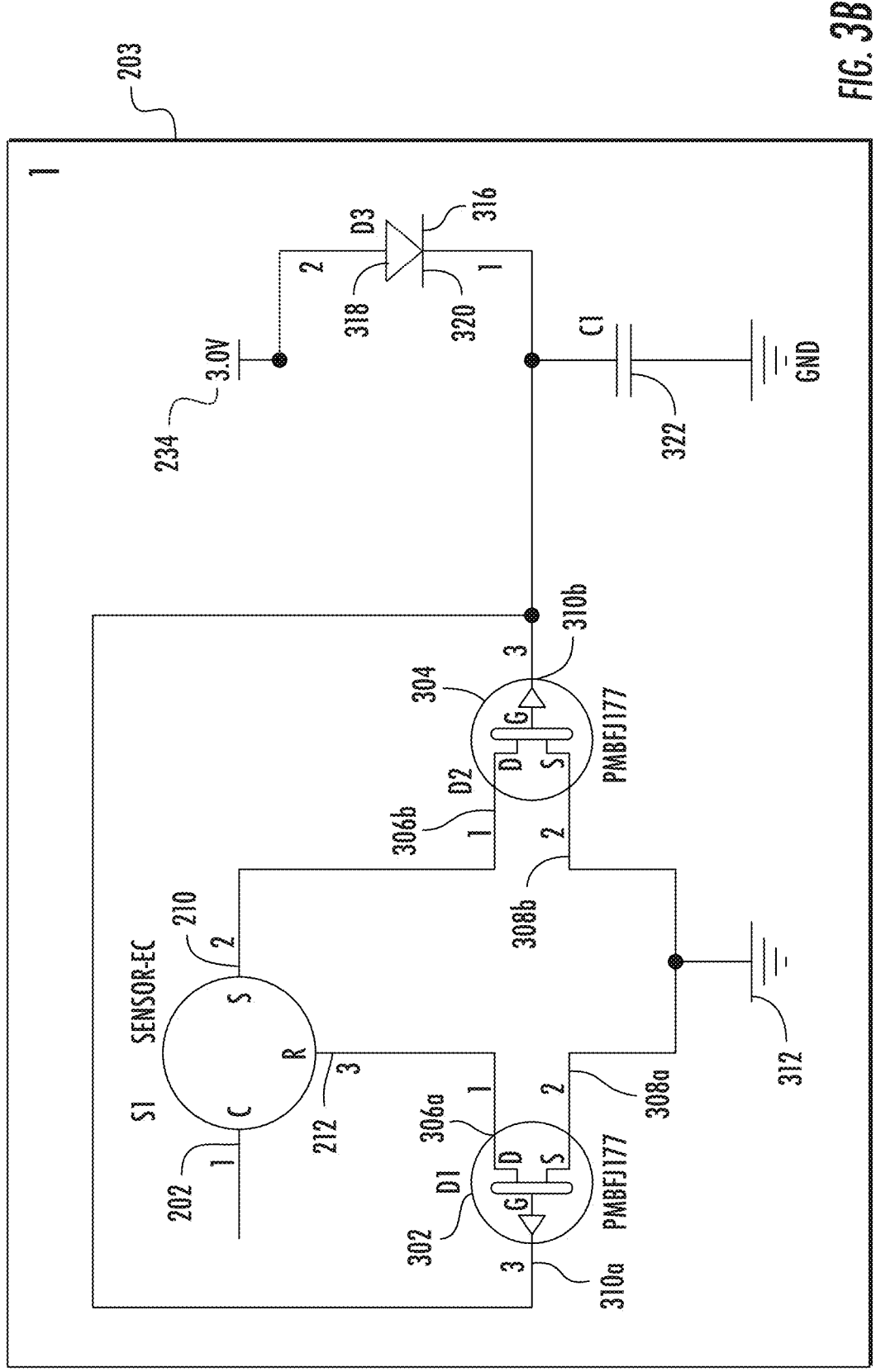
Figure 3C:
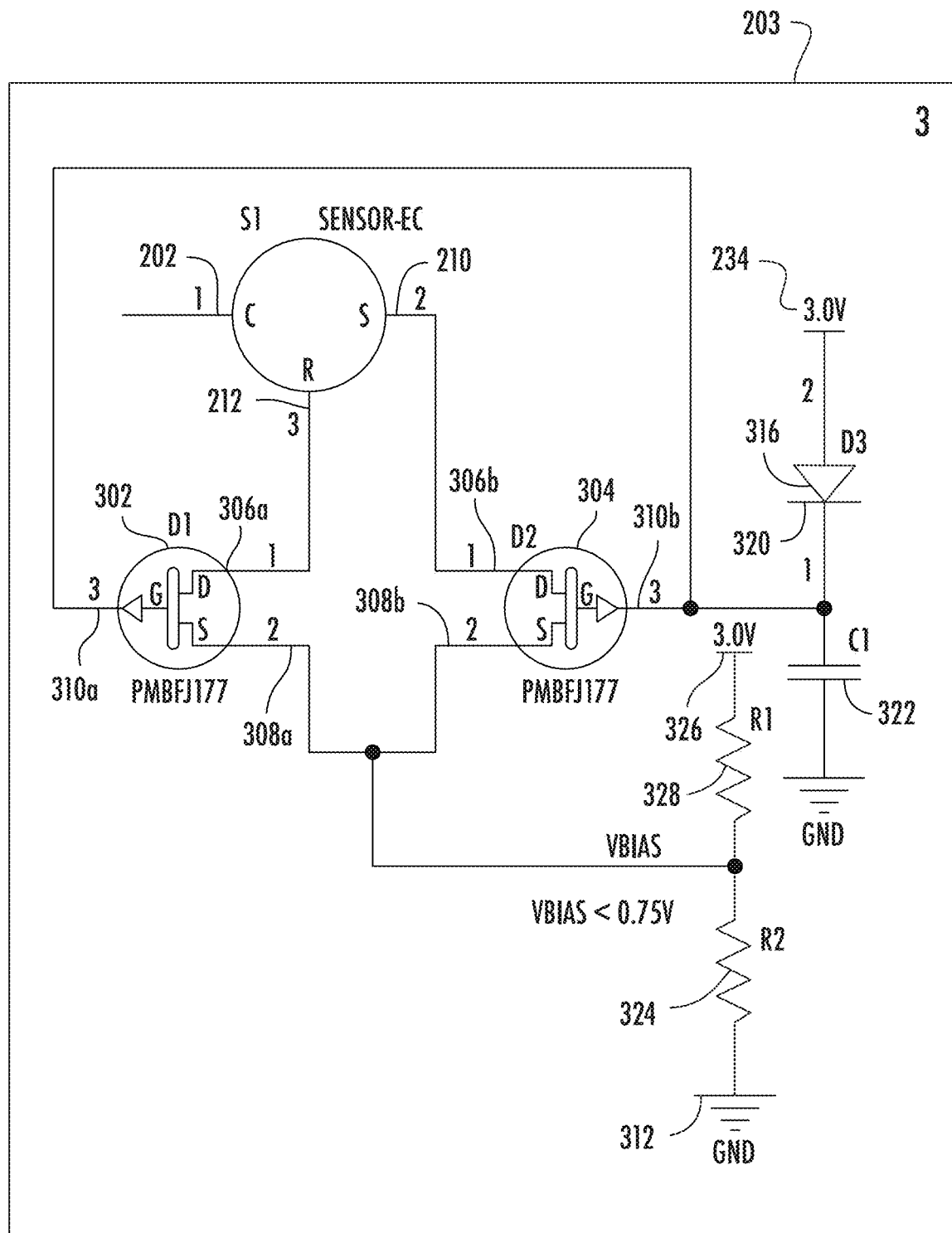

In some embodiments, the electronic circuit 203 may not include the resistive element 314, as is illustrated in FIG. 3b. However, the scope of the disclosure is not limited to embodiments in which the source terminal 308a and 308b of the first transistor 302 and the second transistor 304 are connected to the ground voltage terminal 312. Referring to FIG. 3c, in some alternative embodiments, the source terminal 308a and 308b of the first transistor 302 and the second transistor 304 may be connected to the ground voltage terminal 312 through a second resistive element 324. Additionally, the source terminal 308a and 308b of the first transistor 302 and the second transistor 304, respectively can be connected to a fourth voltage source 326 through a third resistive element 328. In some embodiments, the fourth voltage source 326 may be configured to supply the bias voltage to the source terminals 308a and 308b of the first transistor 302 and the second transistor 304, respectively. In some embodiments, the magnitude of the bias voltage supplied by the fourth voltage source 326 can be the same as or similar to the magnitude of the bias voltage applied at the sensing terminal 210 and the reference terminal 212 of the electrochemical gas sensor 202 by the measurement and control circuitry 208.

In operation, when the sensing system 200 according to some embodiments is powered ON, the source terminal 308a and 308b of the first transistor 302 and the second transistor 304 may receive the bias voltage from the fourth voltage source 326. In some embodiments for which the magnitude of the bias voltage applied at the source terminals 308a and 308b is the same or similar to the magnitude of the bias voltages at the reference terminal 212 and the sensing terminal 210 of the electrochemical gas sensor 202, the flow of leakage current through the first transistor 302 and the second transistor 304 from the electrochemical gas sensor 202 can be reduced.

Further, when the sensing system 200 of some embodiments is powered OFF, the source terminal 308a and 308b can connect to the ground voltage terminal 312. Thereafter, the electronic circuit 203 of such embodiments may operate in a similar manner to the electronic circuit 203 as described above in conjunction with FIG. 3A. For example, when the sensing system 200 is powered OFF, the first transistor 302 and the second transistor 304 can operate in the ON state, which may cause the drain terminal 306a and 306b to connect to, respectively, the source terminals 308a and 308b. Accordingly, the sensing terminal 210 and the reference terminal 212 of such embodiments may connect to the ground voltage terminal 312 (i.e., are grounded).

Figure 3D:
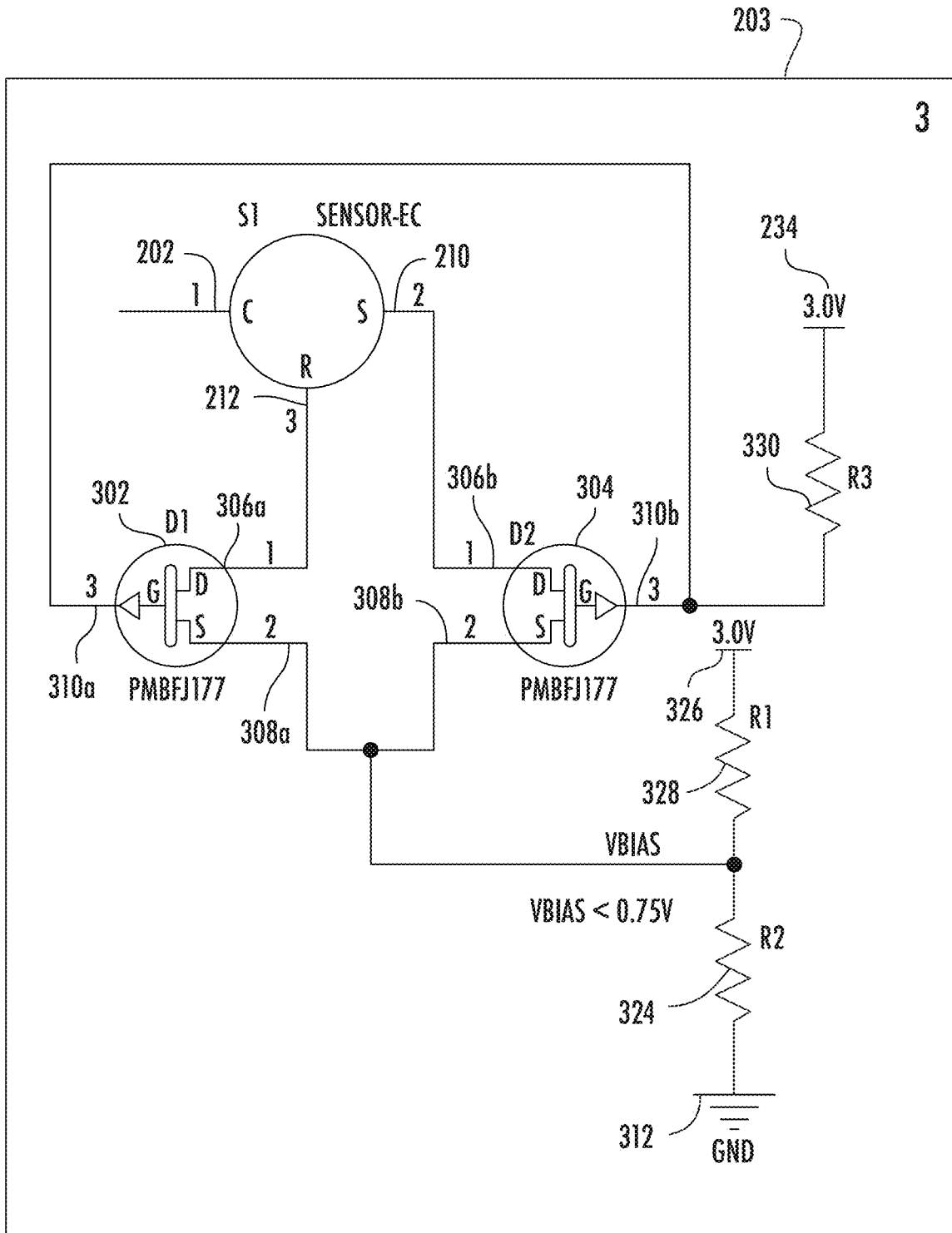

However, the scope of the disclosure is not limited to embodiments for which the gate terminals 310a and 310b are connected to the third voltage source 234 through the diode. In some alternative embodiments, the gate terminals 310a and 310b may be connected to the third voltage source 234 through the fifth resistive element 330, e.g., as illustrated in FIG. 3D. In some examples, the fifth resistive element 330 is optional and the gate terminals 310a and 310b may be directly coupled to the third voltage source 234.

Figure 4:
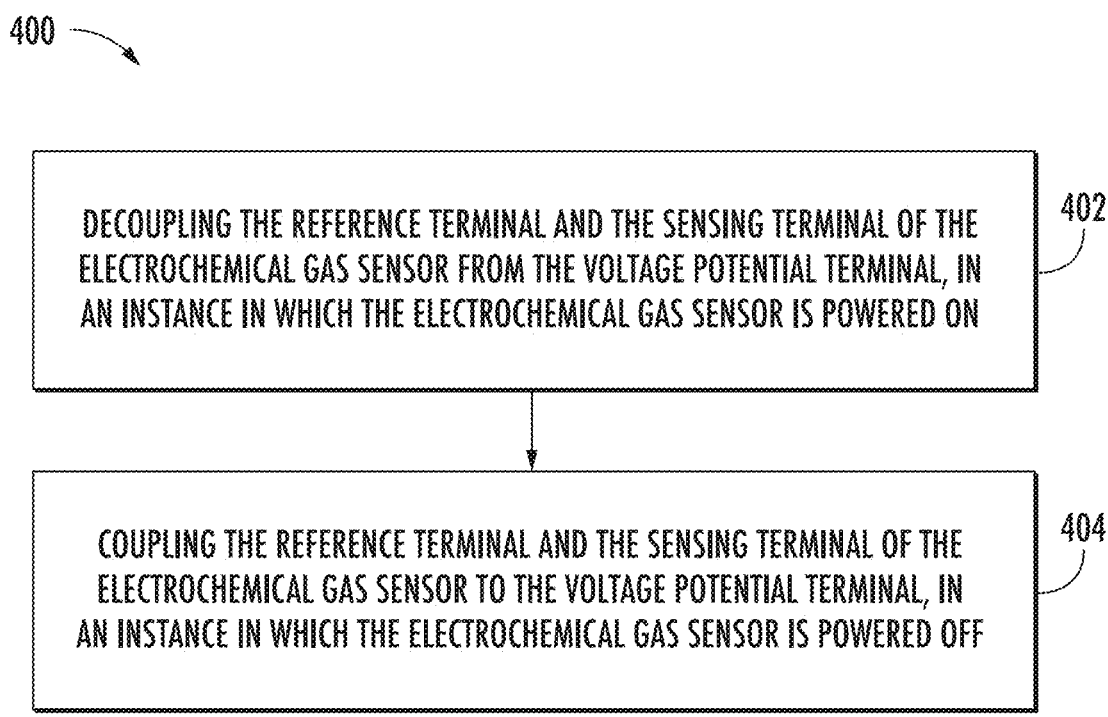
FIG. 4 illustrates a flowchart of a method for operating the electrochemical gas sensor in a sensing system, according to one or more embodiments described herein.

FIG. 4 illustrates a flowchart 400 of a method for operating the electrochemical gas sensor 202 in a sensing system 200, according to some embodiments described herein.

At step 402, the sensing system 200 can include means for decoupling, in an instance in which the sensing system 200 is powered ON, the reference terminal 212 and the sensing terminal 210 of the electrochemical gas sensor 202 from the ground voltage terminal 232. In some embodiments, means for decoupling, as in step 402, can include means, such as the electronic circuit 203, the first switching element 204, the second switching element 206, the first transistor 302, the second transistor 304, and/or the like. As discussed earlier, the first switching element 204 and the second switching element 206 can be NC type switching elements. Accordingly, when the first switching element 204 and the second switching element 206 according to some embodiments receive power, e.g., receive power from the third voltage source 234, the first switching element 204 and the second switching element 206 may operate in the OPEN state, which can cause the decoupling of the reference terminal 212 and the sensing terminal 210 of the electrochemical gas sensor 202 from the ground voltage terminal 232.

At step 404, the sensing system 200 can include means for coupling, in an instance in which the sensing system 200 is powered OFF, the reference terminal 212 and the sensing terminal 210 of the electrochemical gas sensor 202 to the ground voltage terminal 232. In some embodiments, means for coupling, as in step 404, can include means such as the electronic circuit 203-300d, the first switching element 204, the second switching element 206, the first transistor 302, the second transistor 304, and/or the like. As discussed earlier, the first switching element 204 and the second switching element 206 according to some embodiments can be NC type switching elements. According to such embodiments, when the first switching element 204 and the second switching element 206 do not receive power from the third voltage source 234, the first switching element 204 and the second switching element 206 may operate in the CLOSED state, which may cause the coupling of the reference terminal 212 and the sensing terminal 210 to the ground voltage terminal 232.

In some embodiments, one or more of the operations, steps, or processes described herein may be modified or further amplified as described below. Moreover, in some embodiments, additional optional operations may also be included, e.g., in the method of flowchart 400. It should be appreciated that each of the modifications, optional additions, and/or amplifications described herein may be included with the operations previously described herein, either alone or in combination, with any others from among the features described herein.

The provided method description, illustrations, and process flow diagrams are provided merely as illustrative examples and are not intended to require or imply that the steps of the various embodiments must each or all be performed and/or should be performed in the order presented or described. As will be appreciated by one of skill in the art, the order of steps in some or all of the embodiments described may be performed in any order. Words such as "thereafter," "then," "next," etc. are not intended to limit the order of the steps; these words are simply used to guide the reader through the description of the methods. Further, any reference to claim elements in the singular, for example, using the articles "a," "an," or "the" is not to be construed as limiting the element to the singular.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

What is claimed is:

1. An electronic circuit for an electrochemical gas sensor, the electrochemical gas sensor comprising a reference electrode and a sensing electrode, the sensing electrode configured to react with a target gas to generate a current, the electronic circuit comprising:
    a first switching element electrically coupled to a reference terminal of the electrochemical gas sensor and a ground voltage terminal; and
    a second switching element electrically coupled to a sensing terminal of the electrochemical gas sensor and the ground voltage terminal,
    wherein the first switching element comprises a first gate terminal and the second switching element comprises a second gate terminal,
    wherein the first gate terminal is electrically coupled to the second gate terminal, and
    wherein, in an instance in which the electrochemical gas sensor is powered OFF, the first switching element and the second switching element are configured to electrically couple the reference terminal and the sensing terminal to the ground voltage terminal such that the current generated when the sensing electrode and the target gas react while the electrochemical gas sensor is powered OFF flows to the ground voltage terminal and a potential at the reference terminal and the potential at the sensing terminal remain equal.

2. The electronic circuit of claim 1, wherein in an instance in which the electrochemical gas sensor is powered OFF, the first switching element and the second switching element are configured to ground the reference electrode and the sensing electrode of the electrochemical gas sensor via the reference terminal and the sensing terminal, respectively, to the ground voltage terminal.

3. The electronic circuit of claim 1, wherein the first switching element corresponds to a first transistor and the second switching element corresponds to a second transistor.

4. The electronic circuit of claim 3,
    wherein the first transistor comprises a first terminal electrically coupled to the ground voltage terminal, and a second terminal electrically coupled to a reference terminal of the electrochemical gas sensor, and
    wherein the second transistor comprises a third terminal electrically coupled to the ground voltage terminal, and a fourth terminal electrically coupled to a sensing terminal of the electrochemical gas sensor.

5. The electronic circuit of claim 4, wherein the first terminal and the third terminal correspond to a drain terminal, and the second terminal and the fourth terminal correspond to a source terminal.

6. The electronic circuit of claim 4, wherein the first terminal and the third terminal correspond to a source terminal and the second terminal and the fourth terminal correspond to a drain terminal.

7. The electronic circuit of claim 4, wherein
    the first gate terminal and the second gate terminal are electrically coupled to a voltage source and the ground voltage terminal,
    in an instance in which the electrochemical gas sensor is powered OFF, the first gate terminal and the second gate terminal are grounded, causing the first terminal and the third terminal to short with the second terminal and the fourth terminal, respectively, and
    in an instance in which the electrochemical gas sensor is powered ON, the voltage source applies at least a cut-off voltage at the first gate terminal and the second gate terminal, causing the first terminal and the third terminal to disconnect from the second terminal and the fourth gate terminal, respectively.

8. The electronic circuit of claim 4, wherein the first gate terminal and the second gate terminal are electrically coupled to a voltage source through a diode, the diode configured to cause a delay of the electrical coupling of the first gate terminal and the second gate terminal to the voltage source to prevent damage to the electrochemical gas sensor when the electrochemical gas sensor is powered ON.

9. The electronic circuit of claim 4, wherein the first gate terminal and the second gate terminal are electrically coupled with a voltage source through a resistive element or the first gate terminal and the second gate terminal are electrically coupled with the ground voltage terminal through a capacitive element.

10. The electronic circuit of claim 4, wherein
    the first terminal and the third terminal are further coupled to a voltage source, and
    in an instance in which the electrochemical gas sensor is powered ON, the voltage source applies a bias voltage at the first terminal and the third terminal to prevent a leakage current from flowing through the first transistor and the second transistor, respectively, while the electrochemical gas sensor is powered ON, and
    in an instance in which the electrochemical gas sensor is powered OFF, the first terminal and the third terminal are grounded.

11. The electronic circuit of claim 1, wherein the sensing terminal of the electrochemical gas sensor is electrically coupled to a sensing electrode in the electrochemical gas sensor, and the reference terminal of the electrochemical gas sensor is electrically coupled to a reference electrode in electrochemical gas sensor.

12. An apparatus for sensing a target gas, the apparatus comprising:
    an electrochemical gas sensor comprising a reference electrode and a sensing electrode, the sensing electrode configured to generate a current in response to the target gas;
    a first switching element electrically coupled to a reference terminal of the electrochemical gas sensor and a ground voltage terminal; and
    a second switching element electrically coupled to a sensing terminal of the electrochemical gas sensor and the ground voltage terminal, wherein the first switching element comprises a first gate terminal and the second switching element comprises a second gate terminal, wherein the first gate terminal is electrically coupled to the second gate terminal, and wherein, in an instance in which the electrochemical gas sensor is powered OFF, the first switching element and the second switching element are configured to electrically couple the reference terminal and the sensing terminal to the ground voltage terminal such that the current generated when the sensing electrode and the target gas react while the electrochemical gas sensor is powered OFF flows to the ground voltage terminal and a potential at the reference terminal and the potential at the sensing terminal remain equal.

13. The apparatus of claim 12, wherein, in an instance in which the electrochemical gas sensor is powered OFF, the first switching element and the second switching element are configured to ground the reference electrode and the sensing electrode of the electrochemical gas sensor via the reference terminal and the sensing terminal, respectively, to the ground voltage terminal.

14. The apparatus of claim 12, wherein the first switching element comprises a first terminal and a second terminal, the second switching element comprises a third terminal and a fourth terminal, and wherein, in an instance in which the electrochemical gas sensor is powered ON, a voltage source applies at least a cut-off voltage at the first terminal and the second terminal, causing the first terminal and the third terminal to disconnect from the second terminal and the fourth terminal, respectively.

15. The apparatus of claim 14, wherein the first gate terminal and the second gate terminal are electrically coupled to the voltage source through one of a diode or a resistive element.

16. The apparatus of claim 14, wherein the first gate terminal and the second gate terminal are electrically coupled to the ground voltage terminal through a capacitive element.

17. The apparatus of claim 14, wherein the first terminal and the third terminal are electrically coupled to the voltage source, and wherein, in an instance in which the electrochemical gas sensor is powered ON, the voltage source applies a bias voltage at the first terminal and the third terminal to prevent a leakage current from flowing through the first switching element and the second switching element while the electrochemical gas sensor is powered ON.

18. The apparatus of claim 14, wherein, in an instance in which the electrochemical gas sensor is powered OFF, the first terminal and the third terminal are grounded.

19. A method of operating an electronic circuit for an electrochemical gas sensor, the electronic circuit comprising:

a first switching element comprising a first terminal electrically coupled to a ground voltage terminal and a second terminal electrically coupled to a reference terminal of the electrochemical gas sensor; and a second switching element comprising a third terminal electrically coupled to the ground voltage terminal and a fourth terminal electrically coupled to a sensing terminal of the electrochemical gas sensor, the method comprising:

in an instance in which the electrochemical gas sensor is powered ON, disconnecting the reference terminal and the sensing terminal from the ground voltage terminal; and in an instance in which the electrochemical gas sensor is powered OFF, electrically coupling the reference terminal and the sensing terminal to the ground voltage terminal through the first terminal and the third terminal, respectively, such that a potential of the reference terminal and the potential of the sensing terminal are equal.

* * * * *